United States Patent
Felder et al.

(10) Patent No.: US 9,155,582 B2
(45) Date of Patent: Oct. 13, 2015

(54) AIMING INSTRUMENT

(71) Applicant: DEPUY SYNTHES PRODUCTS, LLC, Raynham, MA (US)

(72) Inventors: Martin Felder, Solothurn (CH); Markus Buettler, Solothurn (CH); Stan Kmiec, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 220 days.

(21) Appl. No.: 13/753,954

(22) Filed: Jan. 30, 2013

(65) Prior Publication Data

US 2014/0214045 A1 Jul. 31, 2014

(51) Int. Cl.
| | |
|---|---|
| *A61B 17/58* | (2006.01) |
| *A61B 17/60* | (2006.01) |
| *A61F 2/00* | (2006.01) |
| *A61B 17/92* | (2006.01) |
| *A61B 17/72* | (2006.01) |

(Continued)

(52) U.S. Cl.
CPC .............. *A61B 17/921* (2013.01); *A61B 17/72* (2013.01); *A61B 17/1725* (2013.01); *A61B 17/744* (2013.01); *A61B 17/8897* (2013.01); *A61B 2017/0092* (2013.01); *A61B 2017/00469* (2013.01); *A61B 2017/90* (2013.01); *A61B 2019/5466* (2013.01)

(58) Field of Classification Search
CPC .. A61B 17/921; A61B 17/72; A61B 2017/90; A61B 17/1725; A61B 17/8897; A61B 2019/5466; A61B 17/744; A61B 2017/0092; A61B 2017/00469

USPC ................................. 606/62, 64, 96–98, 104
See application file for complete search history.

(56) References Cited

U.S. PATENT DOCUMENTS

| | | |
|---|---|---|
| 5,403,321 A | 4/1995 | DiMarco |
| 5,478,341 A | 12/1995 | Cook et al. |

(Continued)

FOREIGN PATENT DOCUMENTS

| | | |
|---|---|---|
| DE | 20204126 U1 | 7/2003 |
| WO | WO 2009/052294 A1 | 4/2009 |

(Continued)

OTHER PUBLICATIONS

International Search Report and the Written Opinion of the International Searching Authority, 19 pages, dated Sep. 18, 2014.

(Continued)

*Primary Examiner* — Christopher Beccia
*Assistant Examiner* — Diana S Jones
(74) *Attorney, Agent, or Firm* — Wayne C. Jaeschke, Jr.

(57) ABSTRACT

A device for facilitating implantation of an intramedullary nail includes a coupling portion extending from a first end configured to couple to a proximal end of an intramedullary nail to a joint portion and a radiolucent handle coupled to the joint portion and extending distally therefrom along a path which, when the coupling portion is coupled to an intramedullary nail in a desired orientation, extends substantially parallel to a longitudinal axis of a proximal portion of the nail, the radiolucent part including first and second radiopaque markers positioned and oriented so that, when the nail is coupled to the coupling portion in the desired orientation, the first and second markers align with edges of the proximal portion of the nail.

8 Claims, 14 Drawing Sheets

(51) Int. Cl.
*A61B 17/17* (2006.01)
*A61B 17/74* (2006.01)
*A61B 17/88* (2006.01)
*A61B 17/00* (2006.01)
*A61B 17/90* (2006.01)
*A61B 19/00* (2006.01)

(56) References Cited

U.S. PATENT DOCUMENTS

| | | | |
|---|---|---|---|
| 5,584,838 A | 12/1996 | Rona et al. | |
| 5,620,449 A | 4/1997 | Faccioli et al. | |
| 5,669,915 A | 9/1997 | Caspar et al. | |
| 6,036,696 A | 3/2000 | Lambrecht et al. | |
| 6,074,394 A | 6/2000 | Krause | |
| 6,183,477 B1 | 2/2001 | Pepper | |
| 6,214,013 B1 | 4/2001 | Lambrecht et al. | |
| 6,869,434 B2 | 3/2005 | Choi | |
| 7,033,365 B2 | 4/2006 | Powell et al. | |
| 7,077,847 B2 | 7/2006 | Pusnik et al. | |
| 7,175,633 B2 | 2/2007 | Roth et al. | |
| 7,488,328 B2 | 2/2009 | Gotfried | |
| 7,588,577 B2 | 9/2009 | Fencl et al. | |
| 7,655,009 B2 | 2/2010 | Grusin | |
| 7,727,240 B1 | 6/2010 | Benton | |
| 7,753,913 B2 | 7/2010 | Szakelyhidi, Jr. et al. | |
| 7,776,047 B2 | 8/2010 | Fanger et al. | |
| 7,785,330 B2 | 8/2010 | Sherman et al. | |
| 7,815,647 B2 | 10/2010 | Volzow | |
| 7,819,879 B2 | 10/2010 | Penenberg | |
| 7,837,689 B2 | 11/2010 | Leyden et al. | |
| 7,901,410 B2 | 3/2011 | Bigdeli-Issazadeh et al. | |
| 7,914,532 B2 | 3/2011 | Shaver et al. | |
| 7,935,123 B2 | 5/2011 | Fanger et al. | |
| 8,025,666 B2 | 9/2011 | Roth et al. | |
| 8,034,056 B2 | 10/2011 | Fencl et al. | |
| 8,142,433 B2 | 3/2012 | Volzow | |
| 8,187,281 B2 | 5/2012 | Cresina et al. | |
| 8,206,389 B2 | 6/2012 | Huebner et al. | |
| 8,216,237 B2 | 7/2012 | Edwards et al. | |
| 8,231,629 B2 | 7/2012 | Lerner et al. | |
| 8,241,286 B2 | 8/2012 | Metzinger et al. | |
| 8,257,361 B2 | 9/2012 | Ritchey et al. | |
| 8,257,409 B2 | 9/2012 | Schlienger et al. | |
| 2003/0074005 A1* | 4/2003 | Roth et al. | 606/99 |
| 2005/0203520 A1* | 9/2005 | Volzow | 606/62 |
| 2006/0064106 A1* | 3/2006 | Fernandez | 606/98 |
| 2010/0152740 A1* | 6/2010 | O'Reilly et al. | 606/87 |
| 2011/0054474 A1* | 3/2011 | Metzinger et al. | 606/64 |

FOREIGN PATENT DOCUMENTS

WO  WO 2011/028520 A2  3/2011
WO  WO 2012/162608 A1  12/2012

OTHER PUBLICATIONS

"Zimmer Natural Nail System", Zimmer/Trauma, 24 sheets, 2009.
"Gamma3 Trochanteric Nail 180", Operative Technique, Stryker, 48 sheets, 2005.

* cited by examiner

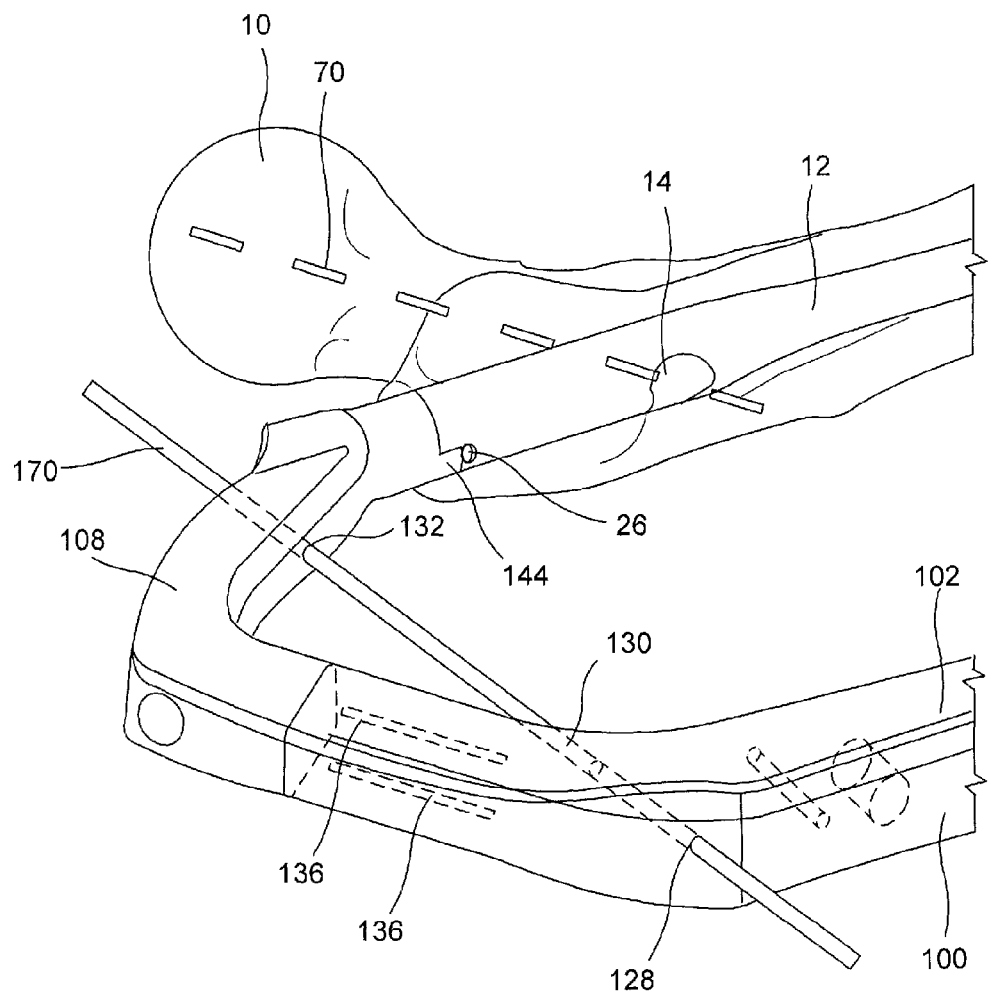
F I G. 17

AIMING INSTRUMENT

BACKGROUND INFORMATION

Fractures are often treated with screws or other fixation devices inserted into or through a bone to stabilize fractured portions thereof once they have been brought into corrective alignment. Trochanteric bone fixation treatments often comprise the insertion of an intramedullary nail into a medullary cavity of a bone and a subsequent insertion of a bone fixation nail into a condylar portion of the bone at an angle relative to the intramedullary nail. Once implanted conventional trochanteric bone fixation devices permit medial and lateral migration of the bone fixation nail within and sometimes out of an outer periphery of the bone. Furthermore, conventional bone fixation devices comprise multiple elements that add to the complexity of bone fixation procedures while minimizing the degree of adjustability of the components relative to one another. Accordingly, this prevents the tailoring of these bone fixation devices to individual requirements of various patients. Such systems therefore reduce the anchoring strength of the bone fixation devices increasing the likelihood of further fractures or other complications.

SUMMARY OF THE INVENTION

The present invention is directed to a device for facilitating implantation of an intramedullary nail. The device comprises a coupling portion extending from a first end configured to couple to a proximal end of an intramedullary nail to a joint portion and a radiolucent handle coupled to the joint portion and extending distally therefrom along a path which, when the coupling portion is coupled to an intramedullary nail in a desired orientation, extends substantially parallel to a longitudinal axis of a proximal portion of the nail, the radiolucent part including first and second radiopaque markers positioned and oriented so that, when the nail is coupled to the coupling portion in the desired orientation, the first and second markers align with edges of the proximal portion of the nail.

BRIEF DESCRIPTION OF THE DRAWINGS

FIG. 17 shows a perspective view of the device of FIG. 1 in a first operative configuration'

DETAILED DESCRIPTION

Figure 1:
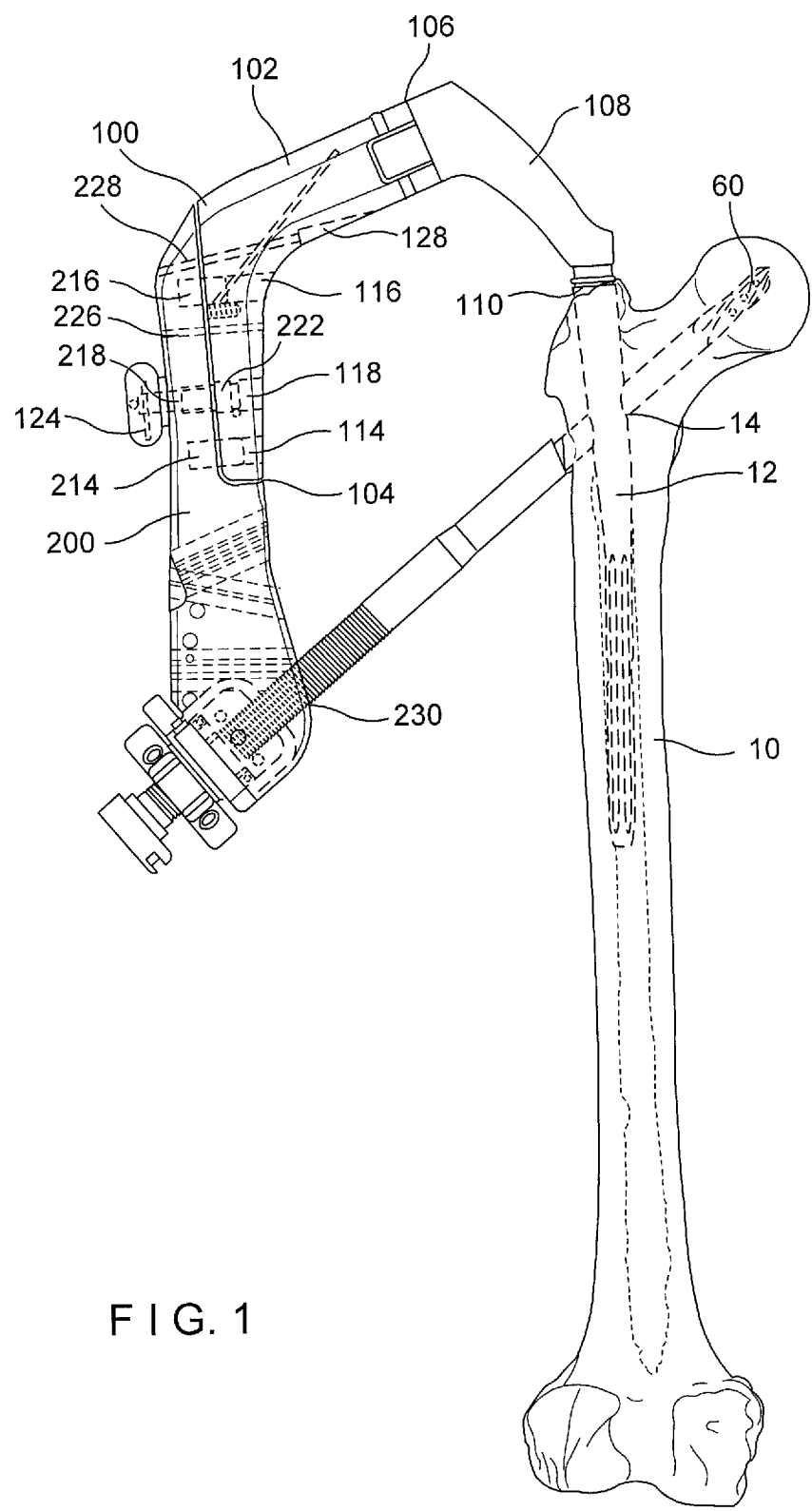
FIG. 1 shows a first perspective view of a bone fixation system according to a first exemplary embodiment of the present invention.
Figure 2:
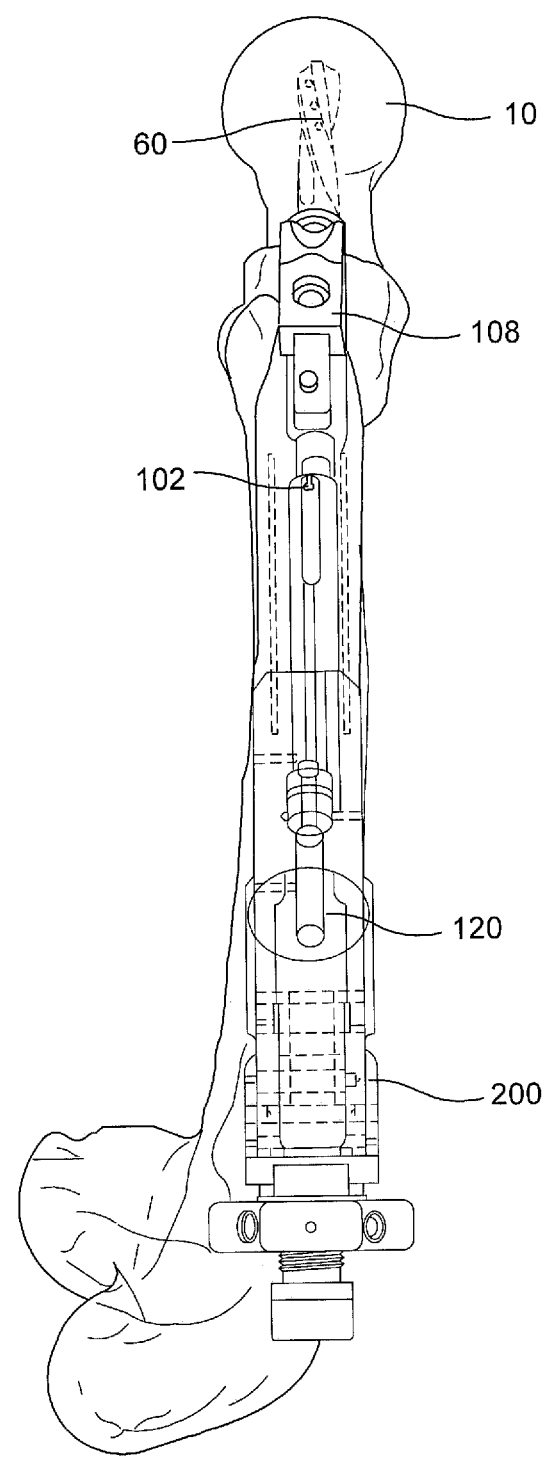
FIG. 2 shows a second perspective view of the device of FIG. 1.
Figure 3:
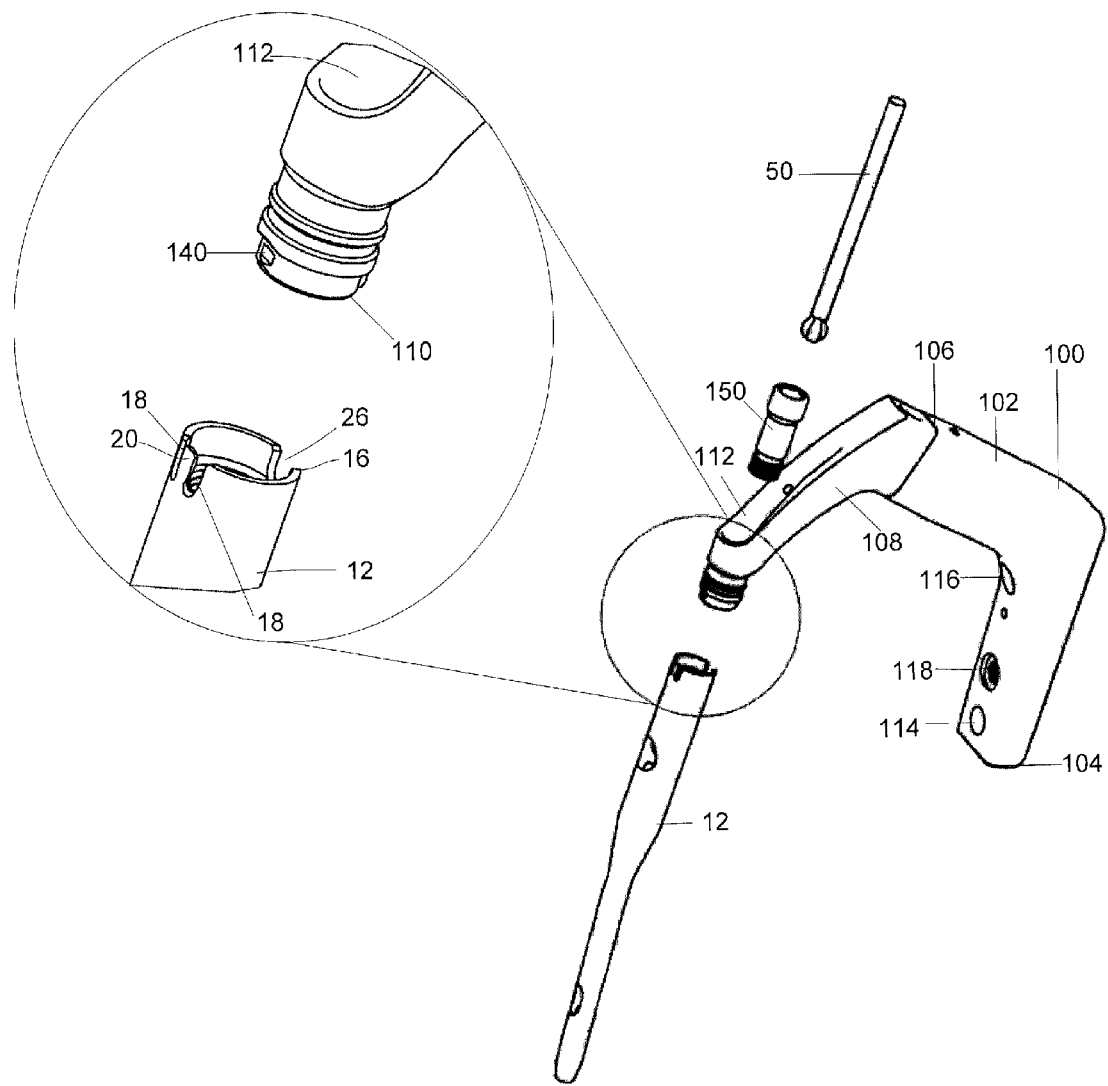
FIG. 3 shows a partial-zoom view of an aiming instrument of the device of FIG. 1.
Figure 4:
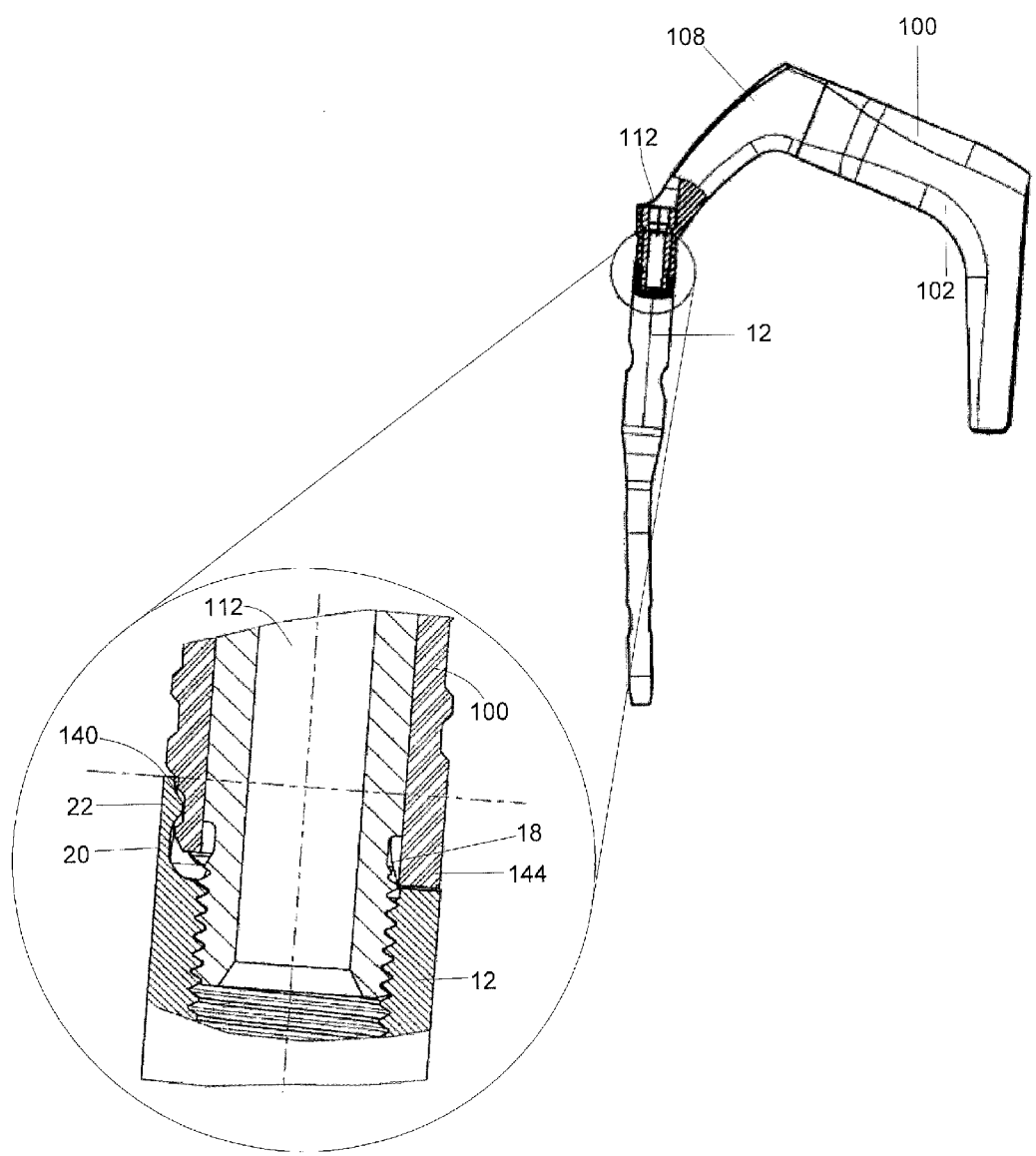
FIG. 4 shows a partial cross-sectional zoom view of the aiming instrument of the device of FIG. 1.

The present invention may be further understood with reference to the following description and the appended drawings. The present invention relates generally to devices and methods for the fixation and stabilization of intertrochanteric fractures. It is noted that although embodiments of the present invention have been described with respect to particular bones, the present invention may also be employed in any other bone fixation procedures including, but not limited to, the fixation of femoral fractures and fractures of other long bones or any other bone in the body. The present invention relates to an aiming instrument for guiding an intramedullary nail into a femur and guiding an insertion of a bone implant (e.g., bone screws, TFNA/PFNA blades, etc.) into any of a plurality of transverse holes extending through the intramedullary nail. The exemplary aiming instrument according to the invention includes a handle portion and a barrel portion, a free end of which engages a proximal end of the intramedullary nail to guide insertion and orientation thereof relative to the bone. The free end of the barrel portion according to the invention is provided with a snap-fit design to temporarily retain a position of the intramedullary nail thereagainst prior to insertion of a connection screw therein. However, those skilled in the art will understand that other coupling mechanisms may be employed without departing from the scope of the invention. The aiming instrument according to the invention also includes a transverse opening guiding the insertion of a guide wire therethrough and over a target portion of the bone in a target position relative to a transverse opening axis of the intramedullary nail. The guide wire inserted through the aiming instrument guides positioning of the intramedullary nail into the bone so that the transverse opening axis thereof is aligned with a median axis of the head-neck region of the bone. The aiming instrument also comprises a pair of radiopaque markers embedded therewithin which, when images of the bone and nail are taken (e.g., X-ray images) aid in determining a correct orientation of the intramedullary nail relative to a neck of the bone and of an insertion path through the nail along which an implant will be inserted into the head-neck region of the bone. The aiming instrument is removably attachable to an aiming arm to permit proximal locking of the intramedullary nail (e.g., inserting an implant through the femoral neck into the head of the femur), as will also be described in greater detail later on.

As shown in FIGS. 1-4 and 10-11, an aiming instrument 100 according to the invention comprises a handle portion 102 extending from a first free end 104 to a second end 106 and a barrel portion 108 extending from the second end 106 of the handle portion 102 to a third free end 110. The aiming instrument 100 is removably attachable to an aiming arm 200, as will be described in greater detail later on. As shown in the partial cross-sectional view of FIG. 10, the handle portion 102 includes a recess 103 which may interlock with a protrusion 109 of the barrel portion 108. In an operative configuration, the protrusion 109 may be permanently secured within the recess 103 via any permanent attachment means (e.g., welding, adhesive, etc.). A pin 111 may also be inserted into a pin hole 113 to lock the handle portion 102 to the barrel portion 108. The handle portion 102 may be formed of carbon fiber reinforced PEEK or another radiolucent material to permit visualization of markers 136 embedded therewithin, as will be described in greater detail later on. The barrel portion 108 may be formed of a more rigid metal material such as steel as this portion may be radiopaque if desired.

The free end 110 of the aiming instrument 100 includes an opening 112 extending therethrough, an axis of the opening 112 being substantially aligned with a longitudinal axis of the bone 10 in an operative configuration so that a connecting screw 150 inserted therethrough aligns with an opening 18 extending into a proximal portion of the intramedullary nail 12.

The handle portion 102 of the aiming instrument includes first and second alignment holes 114, 116 extending transversely therethrough and configured to aid in alignment of the aiming instrument 100 with first and second alignment pins 214, 216 mounted in an aiming arm 200 removably attachable thereto. Specifically, in an operative configuration, pins 214, 216 may be fixedly mounted into the aiming arm 200 and inserted into the respective first and second alignment holes 114, 116 to ensure a proper alignment therewith. In another embodiment, the pins 214, 216 may be removably mounted in the aiming arm 200. The first and second alignment pins 214, 216 of the aiming arm 200 may, if desired, extend only partially through the aiming arm 200. In another embodiment, however, the first and second alignment pins 214, 216 may extend completely through the aiming arm 200. It is further noted that the first and second alignment holes 114, 116 may be positioned along any portion of the handle portion 102 without deviating from the scope of the invention.

The handle portion 102 further comprises a threaded locking hole 118 configured to receive a pin (e.g., a threaded locking element) 218 therethrough in an operative configuration, the pin 218 having a threaded shaft 222 and an enlarged diameter head 124 dimensioned to aid in gripping and manipulation thereof by a surgeon or other user. In one embodiment, the head 124 may include a plurality of grooves distributed about an outer surface thereof to aid in gripping. End portions of the locking hole 118 are formed with a larger diameter than an inner portion thereof to aid in insertion of the pin 218 thereinto. Tightening of the pin 218 into the inner portion causes locking of the pin 218 to the handle portion 102. In an operative configuration, when the first and second alignment holes 114, 116 are aligned with the first and second alignment pins 214, 216, the threaded locking hole 118 aligns with the threaded pin 218 mounted in the aiming arm 200. As noted earlier, the aiming arm 200 is attached to the aiming instrument 100 for the fixation of long bones where proximal locking of the bone is required. In cases where proximal locking of the bone is not required, the aiming instrument 200 is not required. It is noted, however, that the aiming arm 200 may also be used for the distal locking of short nails, as those skilled in the art will understand.

Figure 10:
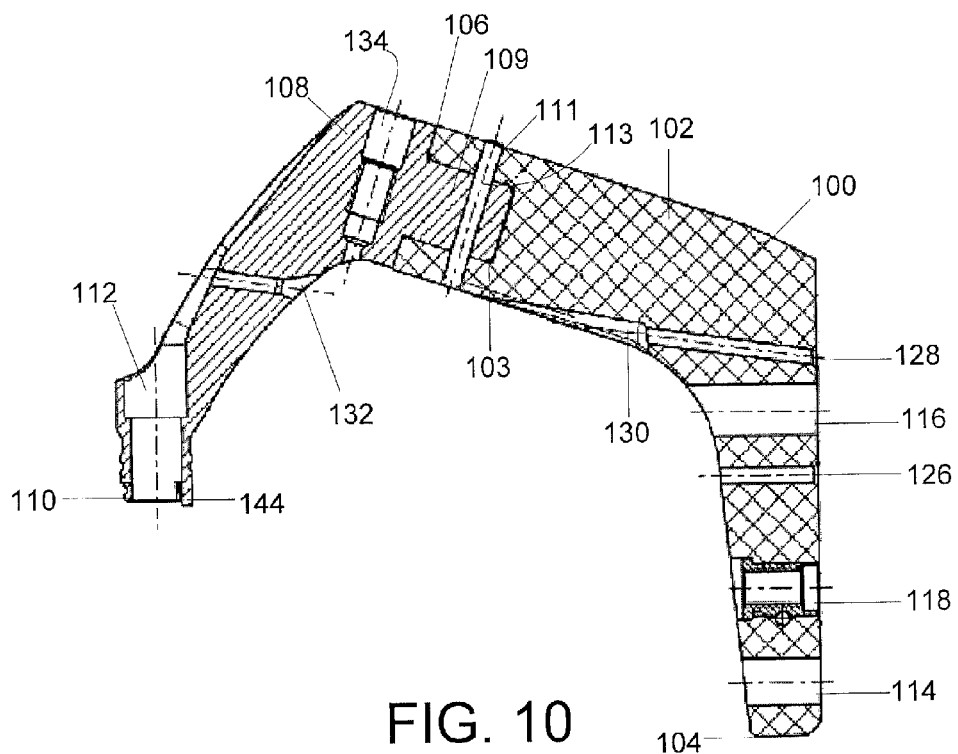
FIG. 10 shows a cross-sectional view of the aiming instrument of FIG. 8.

The handle portion 102 further comprises a first guide wire channel 126 extending therethrough and having a diameter selected to permit insertion of a guide wire therethrough. The first guide wire channel 126 is oriented to receive a guide wire inserted therethrough to aid in positioning of the aiming instrument 100 and optional aiming arm 200 in a target position over the bone 10, as will be described in greater detail below. Specifically, the guide wire (not shown) inserted through the first guide wire channel 126 may be used to identify the proximal end of the intramedullary nail 12. The aiming arm 200 may also comprise a corresponding first guide wire channel 226 extending therethrough and axially aligned with the first guide wire channel 126 in an operative configuration. A second guide wire channel 128 extends through the aiming instrument 100 and includes first and second portions 130, 132 longitudinally separated from one another and extending coaxially with one another. The first portion 130 is formed as an undercut through the handle portion 102 and is open to a side wall thereof, as shown in FIG. 10. In an operative configuration, the second guide wire channel 128 axially aligns with a second guide wire channel 228 of the optional aiming arm 200. It is noted that the first and second guide wire channels 126, 128 are not used at the same time during a surgical procedure. Rather, a guide wire (not shown) inserted through the first guide wire channel 126 is used to identify the proximal end of the nail 12 and subsequently removed therefrom. A guide wire is then inserted through the second guide wire channel 128 to aid in alignment, as will be described in greater detail later on.

The barrel portion 108 includes a transverse opening 134 angled and dimensioned to receive a tool (not shown) which may be hammered to enable hammering of the intramedullary nail 12 into the bone 10, as those skilled in the art will understand.

Figure 11:
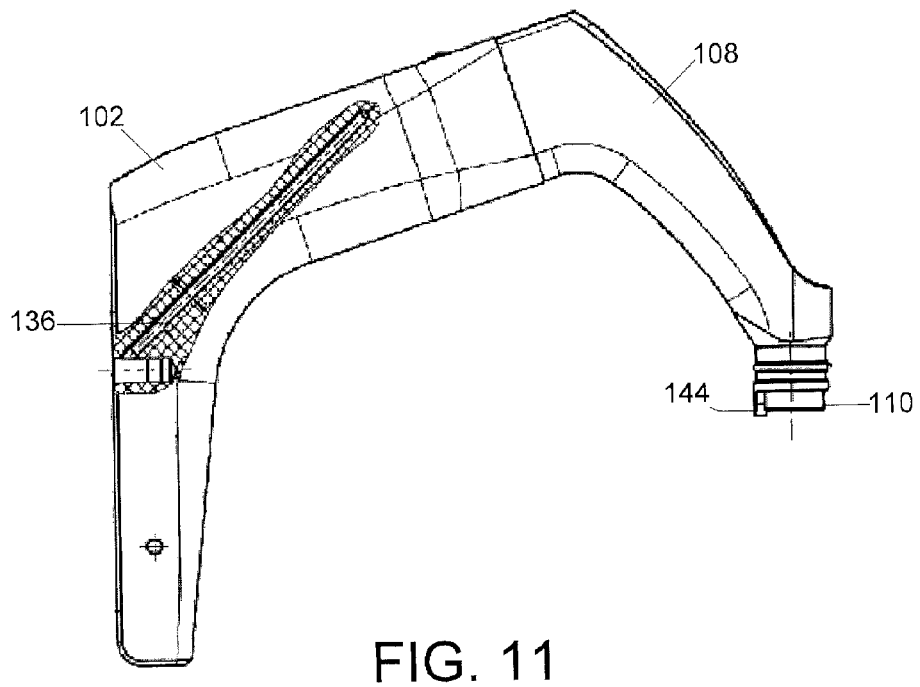
FIG. 11 shows a partial cross-sectional view of the aiming instrument of FIG. 8.
Figure 12:
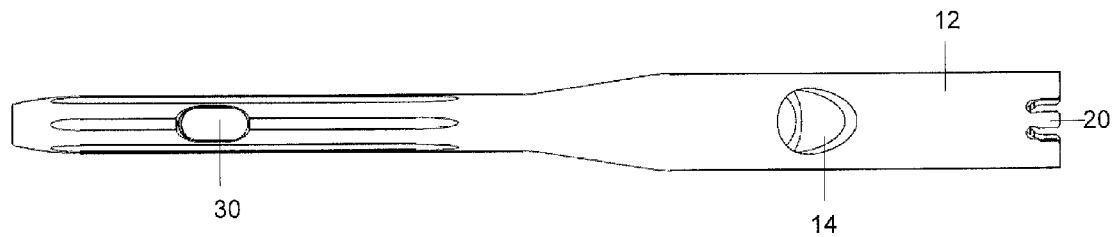
FIG. 12 shows a first perspective of an intramedullary nail of the device of FIG. 1.
Figure 13:
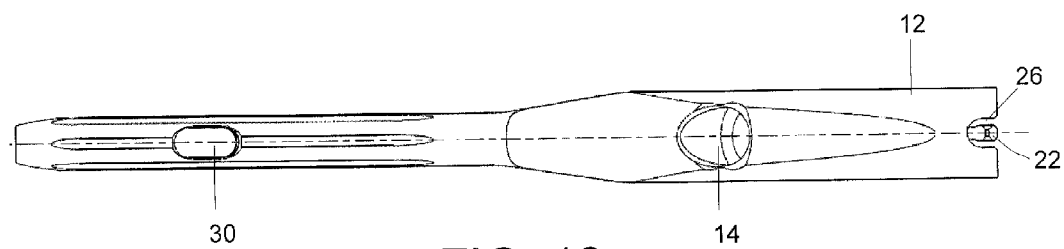
FIG. 13 shows a second perspective of the intramedullary nail of FIG. 12.
Figure 14:
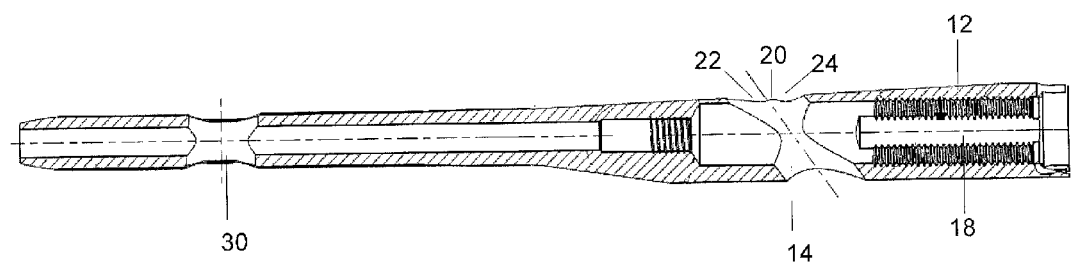
FIG. 14 shows a cross-sectional view of the intramedullary nail of FIG. 12.
Figure 15:
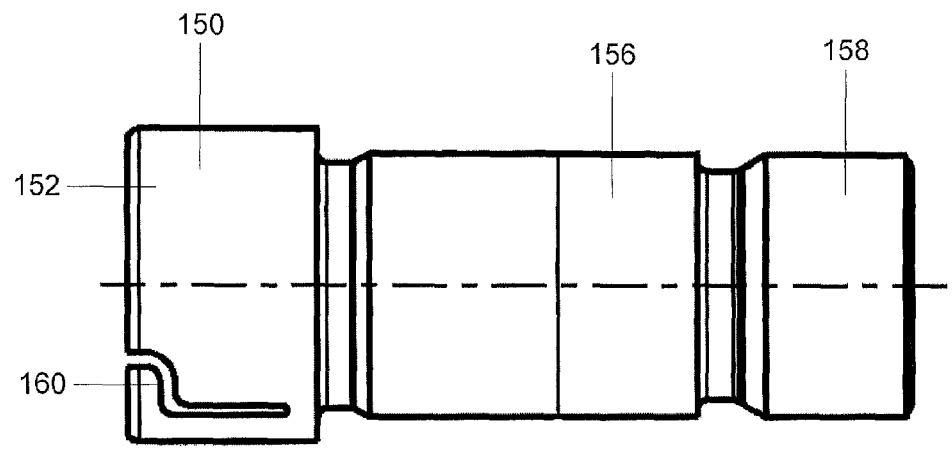
FIG. 15 shows a perspective view of a connecting screw of the device of FIG. 1.
Figure 16:
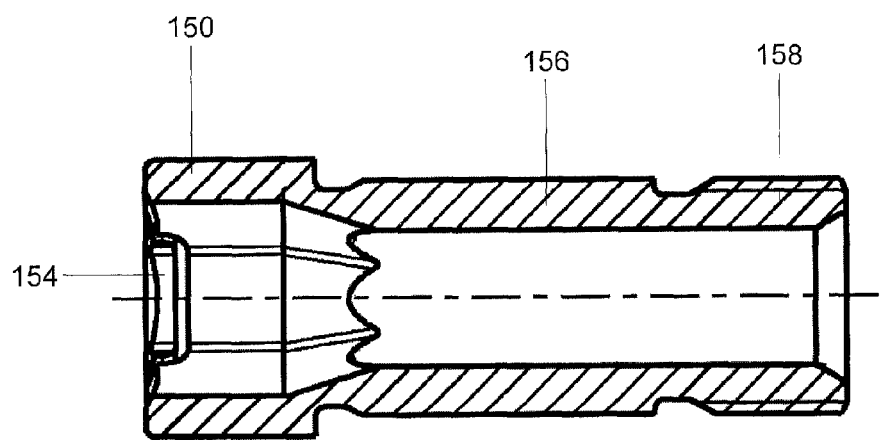
FIG. 16 shows a partial cross-sectional view of the connecting screw of FIG. 15.
Figure 20:
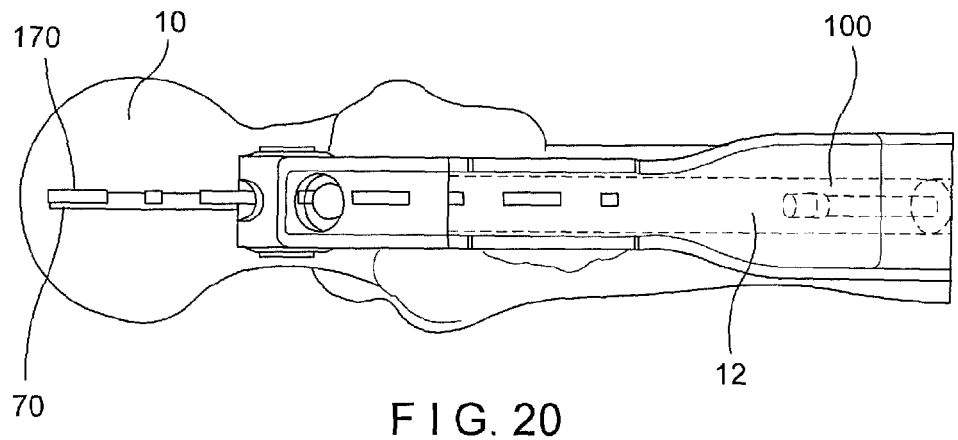
FIG. 20 shows a partial cross-sectional view of the device of FIG. 1 in a properly aligned configuration.
Figure 21:
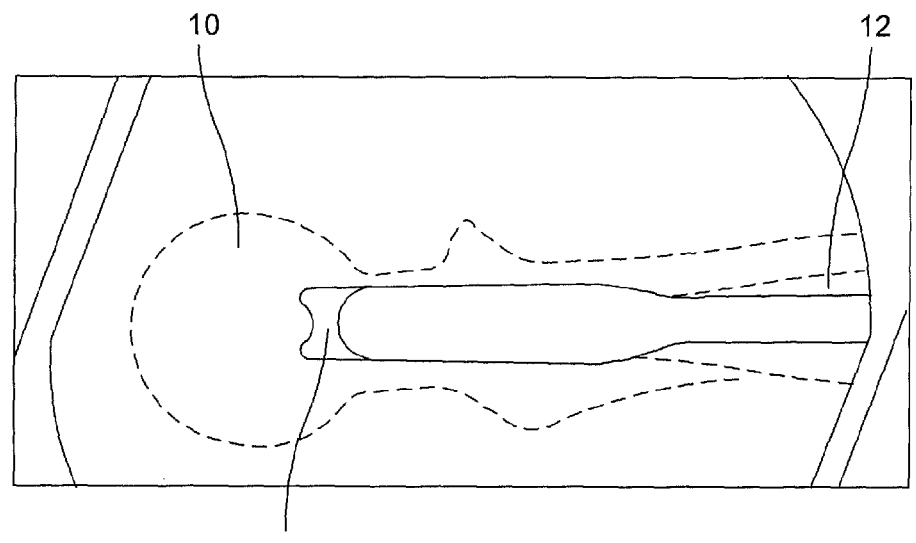
FIG. 21 shows an X-ray of the properly aligned configuration of FIG. 20.

As shown in the partial cross-sectional view of FIG. 11, the handle portion 102 may further comprise a pair of parallel linear radiopaque markers 136 embedded therein. The markers 136 are separated from one another by a distance at least greater than a thickness of a nail to be coupled to the handle portion 102 and each of the markers 136 extends in a plane tangent to a side of a nail coupled to the handle portion 102. As those skilled in the art will understand, this configuration allows for better visibility of the markers 136 under x-ray imaging. Thus, when an axial image of the bone is generated, as shown in FIG. 20, the user may use the markers to obtain a desired rotational orientation of the nail relative to the bone as described in more detail below. The axial image is captured perpendicular to a median axis 70 such that a proximal axis of the bone and the median axis 70 are aligned. As described in more detail below, this desired rotational orientation ensures that an implant 60 inserted through a transverse opening 14 of the nail will pass into the head of the femur along the axis of the femoral neck. The insertion of a guide wire through the second guide wire channel 128 may then be used to double check the rotational alignment of the nail as the guide wire channel 128 is parallel to the axis of the transverse opening 14 of the nail. Thus, when the guide wire extends in the image along the axis of the femoral neck into the center of the femoral head, the rotational orientation of the nail is proper.

Figure 5:
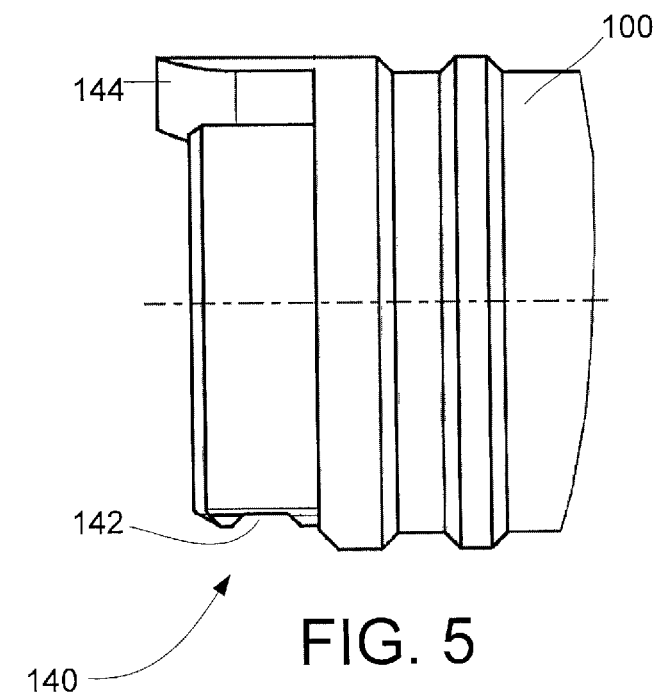
FIG. 5 shows a first partial zoom-view of the aiming instrument of FIG. 1.
Figure 6:
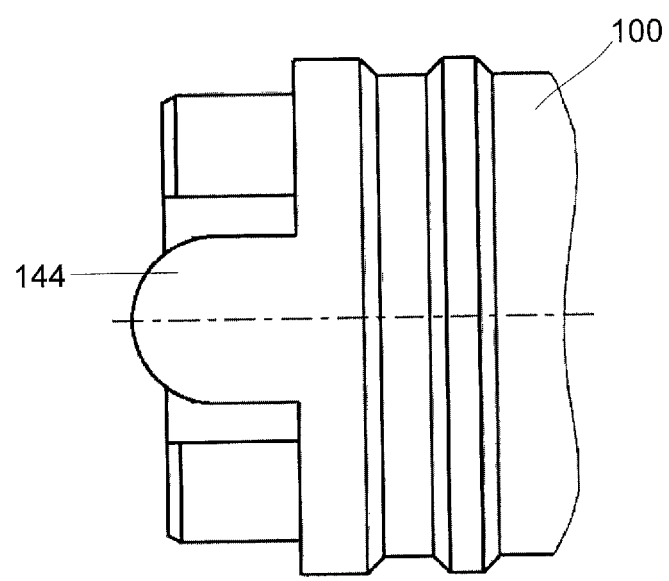
FIG. 6 shows a second partial zoom-view of the aiming instrument of FIG. 5.
Figure 7:
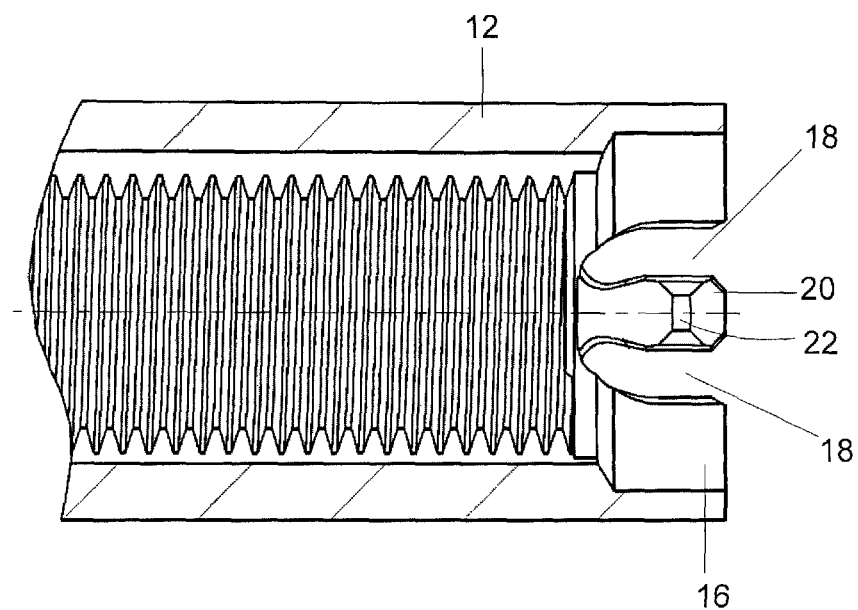
FIG. 7 shows a partial-cross sectional view of the intramedullary nail of FIG. 1.
Figure 8:
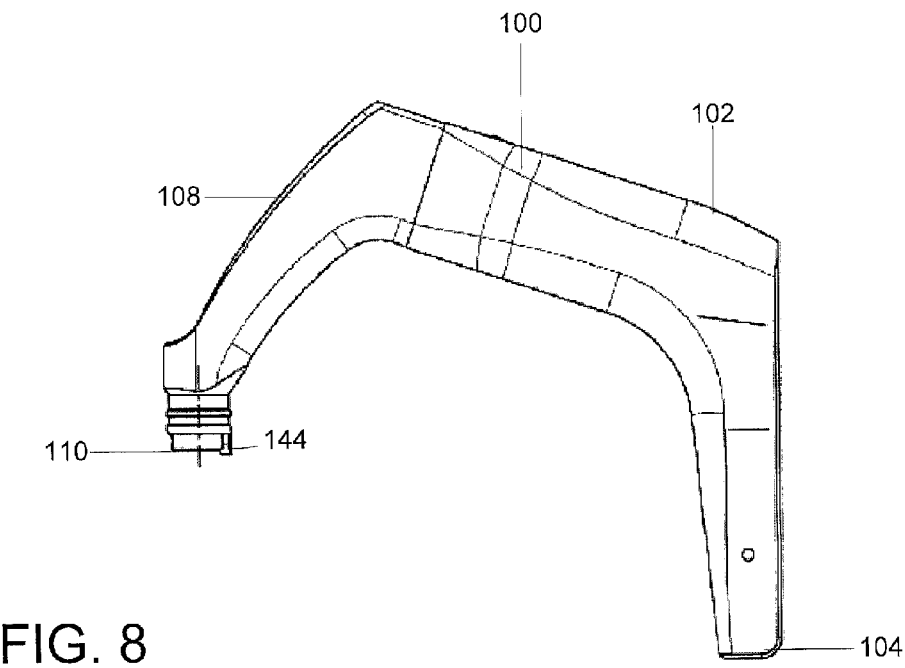
FIG. 8 shows a first side view of the aiming instrument of the device of FIG. 1.
Figure 9:
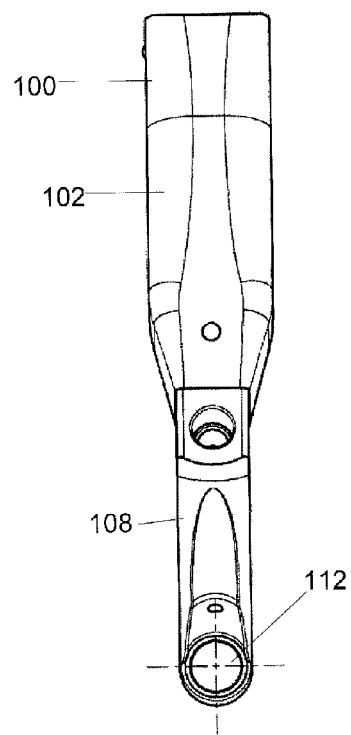
FIG. 9 shows a second side view of the aiming instrument of the device of FIG. 8.

As shown in greater detail in FIGS. 3-7, the free end 110 of the aiming instrument 100 includes a spring mechanism which permits the intramedullary nail 12 to snap into a temporary locking arrangement with the aiming instrument 100. Specifically, as shown in FIGS. 5-7, the free end 100 of the aiming instrument 100 includes a recess 140 configured and dimensioned to engage a tab 20 provided on a proximal end of the intramedullary nail 12. The recess 140 includes a cavity 142 sized and shaped to removably house an increased thickness portion 22 of the tab 20 with a snap-fit engagement. Thus, when the aiming instrument 100 is positioned over the intramedullary nail 12 in a desired orientation, the tab 20 snap-fits into the recess 140 eliminating the need for a user to manually hold the intramedullary nail 12 in place while the connecting screw 150 is inserted into the channel 112. The free end of the aiming instrument 100 further comprises a substantially hemispherical tab 144 sized and shaped for insertion in a corresponding groove 26 formed in a proximal end 16 of the intramedullary nail 12. A length of the tab 144 is equal to or smaller than a length of the groove 26. In an exemplary embodiment, the tab 144 is separated from the recess 140 by approximately 180°. Turning now to the intramedullary nail, as shown in FIG. 7, a first wall portion of a proximal end 16 of the intramedullary nail 12 comprises a pair of cutouts 18 defining the tab 20 therebetween. A width of the tab 20 is selected to permit deflection thereof within a predetermined range of motion relative to the intramedullary nail 12 (i.e., to permit deflection thereof into the cavity 142). A second side wall of the proximal end 16 of the intramedullary nail located approximately 180° from the tab 20 includes the substantially hemispherical cutout 26. Thus, the nail 12 and the aiming instrument 100 may be coupled only when rotated to a desired alignment (i.e., so that the second guide wire channel 128 is in a plane including the transverse opening 14 and longitudinal axis of proximal portion of the nail 12). In an exemplary embodiment, the aiming instrument 100 includes one recess 140 to engage one tab 22. In an alternate embodiment, however, any plurality of recesses 140 may be provided to engage a corresponding number of tabs 22.

The connecting screw 150 according to the invention includes a head 152 with a driver-engaging recess 154 and an elongated shaft 156 extending distally therefrom, a distal portion thereof including threading 158 configured to threadedly engage threading in the intramedullary nail 12, as those skilled in the art will understand. In one embodiment, the connecting screw 150 may include a spring mechanism 160 biased radially inward into the recess 154, the recess 154 being substantially spherical to engage a rounded distal end of a driving mechanism 50. As the rounded distal end is inserted into the recess 154, the spring 160 is moved radially outward against a bias of the spring until a reduced diameter portion of the rounded distal end of the driving mechanism 50 moves past the proximal end of the spring 160 allowing the spring 160 to snap back over the distal end of the driving mechanism 50 locking the driving mechanism to the screw 150. By lockingly engaging the driving mechanism 50 during insertion, disengagement of the connecting screw 150 from the driving mechanism 50 is minimized, thus reducing the time and effort necessary to securely seat connecting screw 150 in the intramedullary nail 12. The connecting screw 150 may be formed substantially similarly to that disclosed in U.S. Application Ser. No. 61/567,390 entitled "Self Holding Feature for a Screw", the entire disclosure of which is incorporated herein by reference.

The intramedullary nail 12 according to the invention may include a bump-cut along an outer periphery of the opening 14 as well as a plurality of cutouts (e.g., facets, etc.) reducing an outer profile of a portion of the 12 nail which resides in a reduced clearance portion of the medullary canal or which is subject to an elevated level of stress during implantation or over the life of the nail. The transverse opening 14 extends from a lateral opening on the first side wall to a medial opening on the second medial wall at a location and angle selected to aim an implant inserted therethrough along an axis of the femoral neck into the head of a femur into which the nail has been implanted. One or more stress reducing features are formed on the periphery of the lateral opening of the transverse hole to diffuse stress concentrations that would otherwise result at these locations enhancing the ability of the device to withstand the cyclic loadings to which it will be subjected. A first stress-reducing feature 20 is formed as a portion of material of the device left in place as first and second regions surrounding the lateral opening are removed (e.g., by milling). Specifically, the first stress-reducing feature 20 is defined between proximal and milled portions 22, 24. The first stress-reducing feature 20 serves as an elastic portion of the nail body capable of straining under excessive loads instead of fracturing. The nail 12 also includes a facet 28 formed as a lateral relief to reduce stress placed on the nail and, consequently, to the bone 10 during insertion. The facet 28 reduces a profile of the nail 12 as it is inserted into the medullary canal with the facet 28 corresponding in location to a portion of the medullary canal which generally includes a curve. The intramedullary nail 12 may further include a transverse hole 30 extending through a distal portion thereof to receive a locking screw, as those skilled in the art will understand. The intramedullary nail 12 according to the invention is substantially similar to that disclosed in greater detail in U.S. Application Ser. No. 61/624,678 entitled "Bump Cut on Hole Edge", the entire disclosure of which is incorporated herein by reference.

Figure 18:
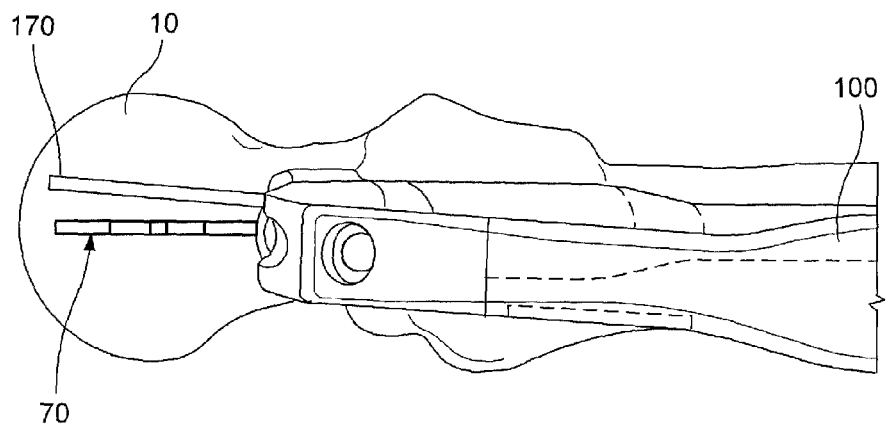
FIG. 18 shows a partial cross-sectional view of the device of FIG. 1 in a misaligned configuration.
Figure 19:
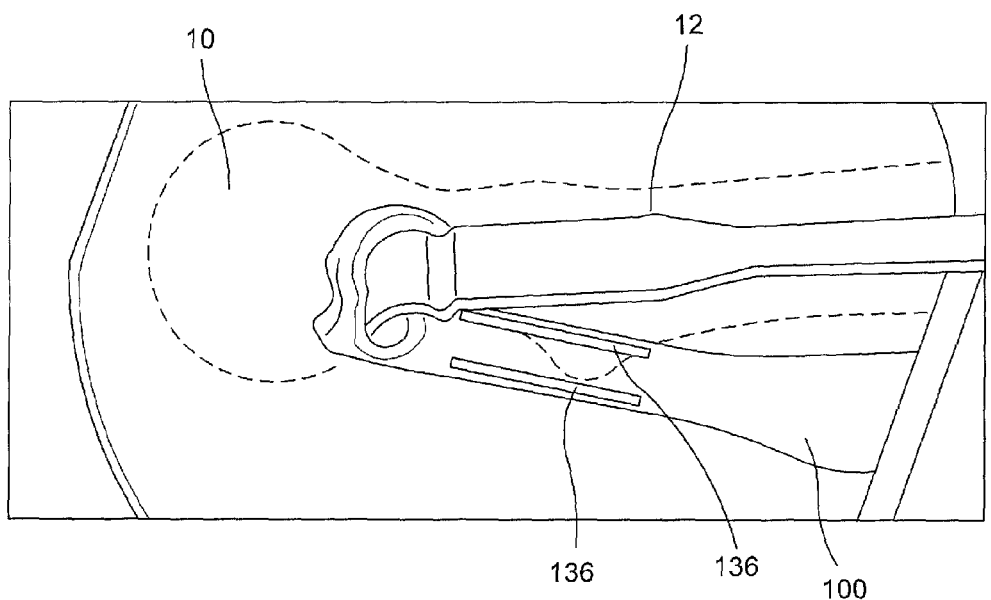
FIG. 19 shows an X-ray of the misaligned configuration of FIG. 18.

FIGS. 17-21 depict an exemplary method according to the invention. In a first exemplary step, the aiming instrument 100 is coupled to an intramedullary nail 12 inserted to a desired depth into the bone 10. If proximal locking of the bone 10 is required, the aiming arm 200 is also attached to the aiming instrument 100. Specifically, pins 214, 216 are inserted through the corresponding first and second alignment holes 114, 116. The pin 218 is inserted through the hole 118 such that the threaded shaft 222 threadedly engages threads of the hole 118. In this configuration, the aiming arm 200 is locked against the aiming instrument 100. An imaging device (e.g., an X-ray machine) is then aligned in a position to obtain a lateral view of the bone (i.e., a view in which a longitudinal axis of a shaft of the bone 10 is congruent with a median axis 70 of the head and neck of the bone). When the proper view has been obtained, a surgeon or other user inserts the intramedullary nail 12 and rotates the nail to ensure that an implant 60 inserted laterally through a traverse opening 14 of the nail 12 will pass into a head of the bone 12 along a desired path along the median axis 70. To achieve a correct orientation, the intramedullary nail 12 may be rotated (via manipulation of the aiming instrument 100) while under observation by a surgeon or other user via an X-ray image until the radiopaque markers 136 are no longer visible in the X-ray but rather, are obscured by the metal material of the intramedullary nail 12 or until the markers 136 extend parallel to edges of the intramedullary nail 12. Specifically, FIGS. 18 and 19 show an incorrect orientation wherein, in FIG. 18, the guide wire 170 is not aligned with the median axis 70. This is evidenced by the visibility of the markers 136 in the X-ray image of FIG. 19. To correct this alignment, the surgeon rotates the nail 12 to the orientation of FIGS. 20-21. In this orientation, the markers 136 extend substantially parallel to edges of the intramedullary nail 12 and are thus no longer visible in the X-ray image of FIG. 21.

Figure 22:
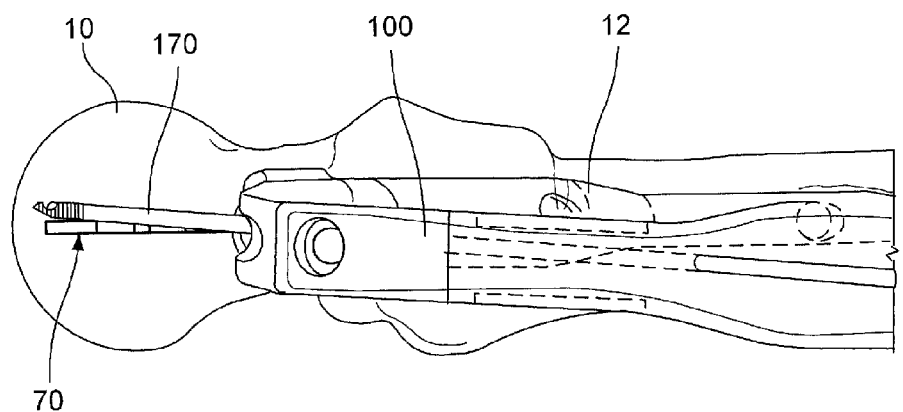
FIG. 22 shows a partial cross-sectional view of the device of FIG. 1 in a misaligned configuration.
Figure 23:
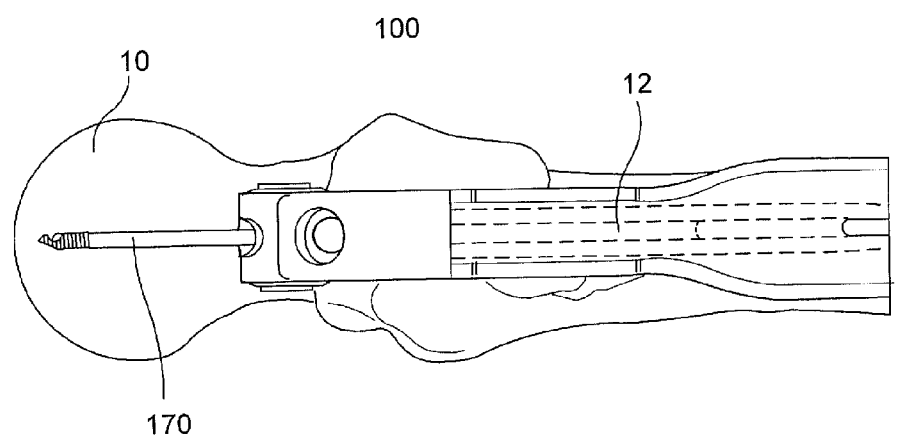
FIG. 23 shows a partial cross-sectional view of the device of FIG. 22 in a properly aligned configuration.

This correct alignment may be verified or independently arrived at by the insertion of a guide wire 170 through the second guide wire channel 128, as shown in FIGS. 22-23. Specifically, the guide wire 170 passes outside the body along a path parallel to the median axis 70 in an axial view, as those skilled in the art will understand. Thus, a lateral X-ray image (not shown) of the bone will show the guide wire 170 extending over the head of the bone 10 and the aiming instrument 100. FIG. 22 depicts the guide wire 170 extending non-parallel to the median axis 70. Consequently, the nail 12 is rotated until the guide wire 170 appears on the X-ray image (not shown) along the desired path of the implant 60 into the head of the bone 10, as shown in FIG. 23.

Once the above alignment has been achieved using one or both of the methods disclosed above, a guide wire (not shown) is inserted through a guide hole 230 of the aiming instrument along the intended insertion path for the implant 60, through the transverse opening 14 in the nail and into the head of the bone 10. Once the guide wire is in place as desired, the implant 60 (e.g., a PFNA blade) is inserted over the guide wire (not shown) into the head-neck region of the bone 10. Accordingly, the device according to the invention permits a guide wire (not shown) to be properly inserted and oriented within the bone 10 on a first attempt.

It will be apparent to those skilled in the art that various modifications and variations may be made in the structure and the methodology of the present invention, without departing from the spirit or scope of the invention. Thus, it is intended that the present invention cover modifications and variations of the invention provided that they come within the scope of the appended claims and their equivalents.

What is claimed is:

1. A device for facilitating implantation of an intramedullary nail, comprising:
   a coupling portion extending from a first end configured to couple to a proximal end of an intramedullary nail to a joint portion;
   a radiolucent handle coupled to the joint portion and extending distally therefrom along a path which, when the coupling portion is coupled to an intramedullary nail in a desired orientation, extends substantially parallel to a longitudinal axis of a proximal portion of the nail, the radiolucent handle including first and second radiopaque markers positioned and oriented so that, when the intramedullary nail is coupled to the coupling portion in the desired orientation, the first and second markers align with edges of the proximal portion of the intramedullary nail;
   a first guide wire hole extending through the radiolucent handle and a second guide wire hole extending through the coupling portion, wherein the first and second guide wire holes are axially aligned with one another; and
   a guide wire insertable through the first and second guide wire holes along a wire axis selected so that, when the intramedullary nail is coupled to the aiming instrument in a desired orientation, the wire axis is in a plane including a longitudinal axis of a proximal portion of the intramedullary nail and an axis of a transverse opening in the intramedullary nail through which an implant is to be inserted into a target portion of a bone.

2. The device of claim 1, further comprising an aiming arm removably attachable to the radiolucent handle, the aiming arm including a guide opening extending therethrough at an angle selected to align with an axis of a transverse opening extending through the proximal portion of the intramedullary nail.

3. The device of claim 2, wherein the handle comprises a first pair of alignment holes aligning with a second pair of alignment holes of the aiming arm.

4. The device of claim 3, further comprising first and second pins received through the first and second pairs of alignment holes to temporarily secure the aiming arm to the intramedullary handle.

5. The device of claim 4, further comprising a locking pin mounted on the aiming arm and insertable into a locking pin hole of the handle to lock the aiming arm thereto.

6. The device of claim 1, wherein the first end of the coupling portion includes a recess engaging a proximal end of the intramedullary nail with a snap-fit engagement.

7. The device of claim 6, wherein the proximal end of the intramedullary nail includes a spring-formed tab.

8. The device of claim 6, wherein the first end further comprises a protrusion extending distally therefrom, the protrusion being sized and shaped to engage a corresponding groove formed in the proximal end of the intramedullary nail, the protrusion being separated from the recess by approximately 180 degrees.

* * * * *